(12) United States Patent
Uchiyama et al.

(10) Patent No.: US 10,126,205 B2
(45) Date of Patent: Nov. 13, 2018

(54) SENSOR

(71) Applicant: ISUZU MOTORS LIMITED, Tokyo (JP)

(72) Inventors: Tadashi Uchiyama, Fujisawa (JP); Naoto Murasawa, Fujisawa (JP); Satoshi Hanawa, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 85 days.

(21) Appl. No.: 15/503,354

(22) PCT Filed: Aug. 11, 2015

(86) PCT No.: PCT/JP2015/072775
§ 371 (c)(1),
(2) Date: Feb. 10, 2017

(87) PCT Pub. No.: WO2016/024591
PCT Pub. Date: Feb. 18, 2016

(65) Prior Publication Data
US 2017/0227423 A1 Aug. 10, 2017

(30) Foreign Application Priority Data

Aug. 11, 2014 (JP) .................................. 2014-163747

(51) Int. Cl.
*G01M 15/10* (2006.01)
*G01N 27/22* (2006.01)

(52) U.S. Cl.
CPC ........ *G01M 15/102* (2013.01); *G01N 27/226* (2013.01)

(58) Field of Classification Search
CPC ...... F01N 2560/05; F01N 11/00; F01N 3/023; G01N 27/226; F02D 41/029; G01M 15/102

See application file for complete search history.

(56) References Cited

U.S. PATENT DOCUMENTS 7,758,676 B2  7/2010 Mital et al.
7,772,855 B2* 8/2010 Sakuma ............. G01N 15/0656
                                            324/693

(Continued)

FOREIGN PATENT DOCUMENTS

CN    101165323 A    4/2008
CN    100549375 C   10/2009

(Continued)

OTHER PUBLICATIONS

Extended European Search Report for related European Patent Application EP15831639.8 dated Jan. 10, 2018; 6 pages.

(Continued)

*Primary Examiner* — Freddie Kirkland, III
(74) *Attorney, Agent, or Firm* — Procopio, Cory, Hargreaves & Savitch LLP (57) ABSTRACT

The sensor includes a filter member including cells that trap PM in exhaust gas; electrode members arranged to face each other with the cell interposed and forming a capacitor, an electric heater that executes, when an amount of PM has accumulated in the cells, filter regeneration of heating the cells to combust and remove the PM, a storage unit that stores a reference reduction amount, which is an electrostatic capacitance reduction amount between the electrode members in a case where the filter regeneration is executed in a state where the PM is not flowing into the filter member, and estimation units that estimate a PM amount based on (a) an actual electrostatic capacitance change amount between the electrode members during a regeneration interval period, and (b) a difference between an actual electrostatic capacitance reduction amount between the electrode members and the reference reduction amount during a filter regeneration period.

6 Claims, 7 Drawing Sheets

(56) References Cited

U.S. PATENT DOCUMENTS

| | | | |
|---|---|---|---|
| 8,845,798 B2* | 9/2014 | Nishijima | F01N 11/00 |
| | | | 204/415 |
| 9,657,666 B2* | 5/2017 | Nishijima | F01N 3/101 |
| 9,846,110 B2* | 12/2017 | Tylutki | G01N 15/0656 |
| 9,988,960 B2* | 6/2018 | Tsukamoto | F02D 41/024 |
| 2008/0087012 A1 | 4/2008 | Konstandopoulos | |
| 2009/0284271 A1 | 11/2009 | Sakuma et al. | |
| 2010/0146935 A1 | 6/2010 | Chen et al. | |
| 2013/0204540 A1 | 8/2013 | Genssle et al. | |
| 2017/0159536 A1* | 6/2017 | Uchiyama | G01N 27/22 |

FOREIGN PATENT DOCUMENTS

| | | |
|---|---|---|
| CN | 102292153 A | 12/2011 |
| DE | 102012201594 A1 | 8/2013 |
| EP | 2014888 A3 | 3/2010 |
| EP | 3159685 A1 | 4/2017 |
| JP | 2008-190502 A | 8/2008 |
| JP | 2010275977 A | 12/2010 |
| JP | 2012-083210 A | 4/2012 |
| JP | 2014015914 A | 1/2014 |
| WO | 2008/096853 A1 | 8/2008 |
| WO | 2011001824 A1 | 1/2011 |

OTHER PUBLICATIONS

International Search Report and Written Opinion for PCT App No. PCT/JP2015/072775 dated Nov. 17, 2015, 7 pgs.
First Office Action for related CN App No. 201580042960.7 dated Jul. 16, 2018, 9 pgs.

* cited by examiner

SENSOR

CROSS-REFERENCE TO RELATED APPLICATIONS

This application is a U.S. National Stage entry of PCT Application No. PCT/JP2015/072775, filed on Aug. 11, 2015, which claims priority to Japanese Patent Application No. 2014-163747, filed Aug. 11, 2014, the contents of which are incorporated herein by reference.

TECHNICAL FIELD

The present invention relates to a sensor and more particularly to a PM sensor which detects particulate matter (hereinafter, referred to as PM) included in exhaust gas,

BACKGROUND ART

Conventionally, an electrical resistance-type PM sensor that detects PM in an exhaust gas discharged from an internal combustion engine has been known. In general, the electrical resistance-type PM sensor has a pair of conductive electrodes arranged to face each other on a surface of an insulation substrate and estimates a PM amount by using a change in an electrical resistance value caused due to conductive PM (mainly, soot component) attached to the electrodes (for example, refer to Patent Document 1).

PRIOR ART LITERATURE

Patent Literature

Patent Document: JP-A-2012-83210

SUMMARY OF THE INVENTION

Problem that the Invention is to Solve

Since the electrical resistance-type PM sensor has a simple structure in Which the PM is attached to each of the electrodes, there is a possibility that some of the PM attached to the electrodes may be detached in a driving state where an exhaust flow rate increases. In this case, it is not possible to ensure the estimation precision. Also, since the electrical resistance value between the electrodes does not change until the electrodes are interconnected by accumulation of the PM, it is not possible to accurately estimate the PM amount until the electrodes are interconnected by the PM. Further, since the electrical resistance value between the electrodes does not change during a regeneration period in which the PM accumulated between the electrodes is combusted and removed by an electrical heater, it is also not possible to estimate the PM amount during the regeneration period.

For this reason, the electrical resistance-type PM sensor cannot continuously estimate the amount of PM that is discharged from the engine, and a utility thereof is limited to a utility of diagnosing on board a failure at a more downstream side than a Diesel Particulate Filter (hereinafter, referred to as DPF).

The present invention has been made in view of the above situations, and an object thereof is to provide a PM sensor capable of continuously estimating a PM amount included in an exhaust gas.

Means for Solving the Problem

A sensor of the disclosure includes: a porous filter member including a plurality of cells that traps particulate matter in exhaust gas; at least a pair of electrode members arranged to face each other with the cell being interposed therebetween and forming a capacitor; regeneration means that executes, when a predetermined amount of particulate matter has accumulated in the cell, filter regeneration of heating the cell to combust and remove the accumulated particulate matter; storage means that stores therein a reference reduction amount, which is an electrostatic capacitance reduction amount between the pair of electrode members in a case where the filter regeneration has been executed by the regeneration means in a state where the exhaust gas including the particulate matter is not flowing into the filter member; and estimation means that estimates a particulate matter amount included in the exhaust gas based on an actual electrostatic capacitance change amount between the pair of electrode members during a regeneration interval period from an end of the filter regeneration by the regeneration means to a start of a next filter regeneration, and estimates the particulate matter amount included in the exhaust gas based on a difference between an actual electrostatic capacitance reduction amount between the pair of electrode members and the reference reduction amount during a filter regeneration period by the regeneration means.

MODE FOR CARRYING OUT THE INVENTION

Hereinafter, PM sensors in accordance with respective illustrative embodiments of the present invention will be described with reference to the accompanying drawings. The same components are denoted with the same reference numerals, and the names and functions thereof are the same. Therefore, the detailed descriptions thereof will not be repetitively made.

[First illustrative Embodiment]

Figure 1:
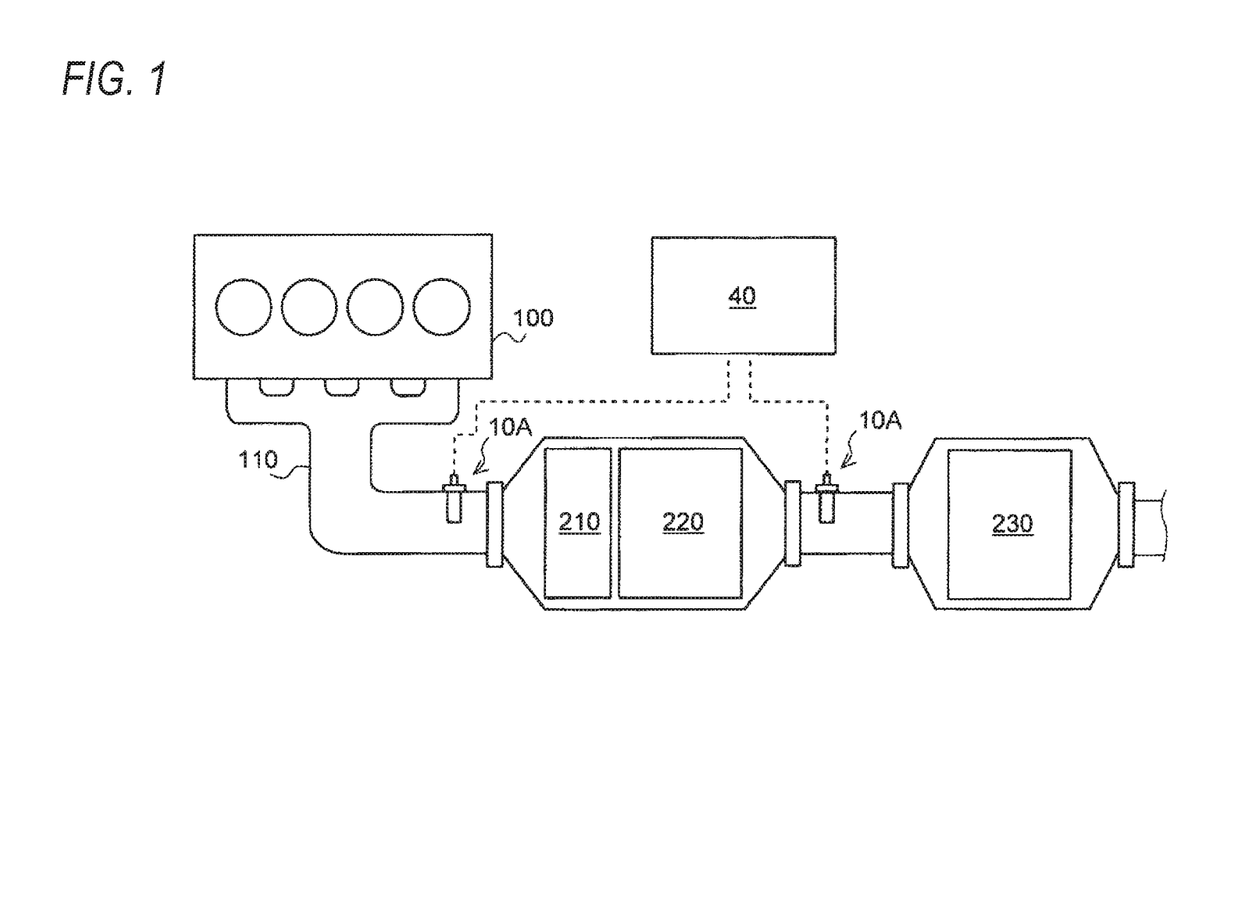
FIG. 1 is a schematic configuration view depicting an example of an exhaust system to which a PM sensor of a first illustrative embodiment is applied.

FIG. 1 is a schematic configuration view depicting an example of an exhaust system of a Diesel engine (hereinafter, simply referred to as 'engine') 100 to which a PM sensor 10A of a first illustrative embodiment is applied. An exhaust pipe 110 is provided with an oxidation catalyst 210, a DPF 220, a NOx purification catalyst 230 and the like in corresponding order from an exhaust upstream side. In the first illustrative embodiment, the PM sensor 10A may be provided to the exhaust pipe 110 at an upstream side of the DPF 220 or to the exhaust pipe 110 at a downstream side of the DPF 220.

Figure 2:
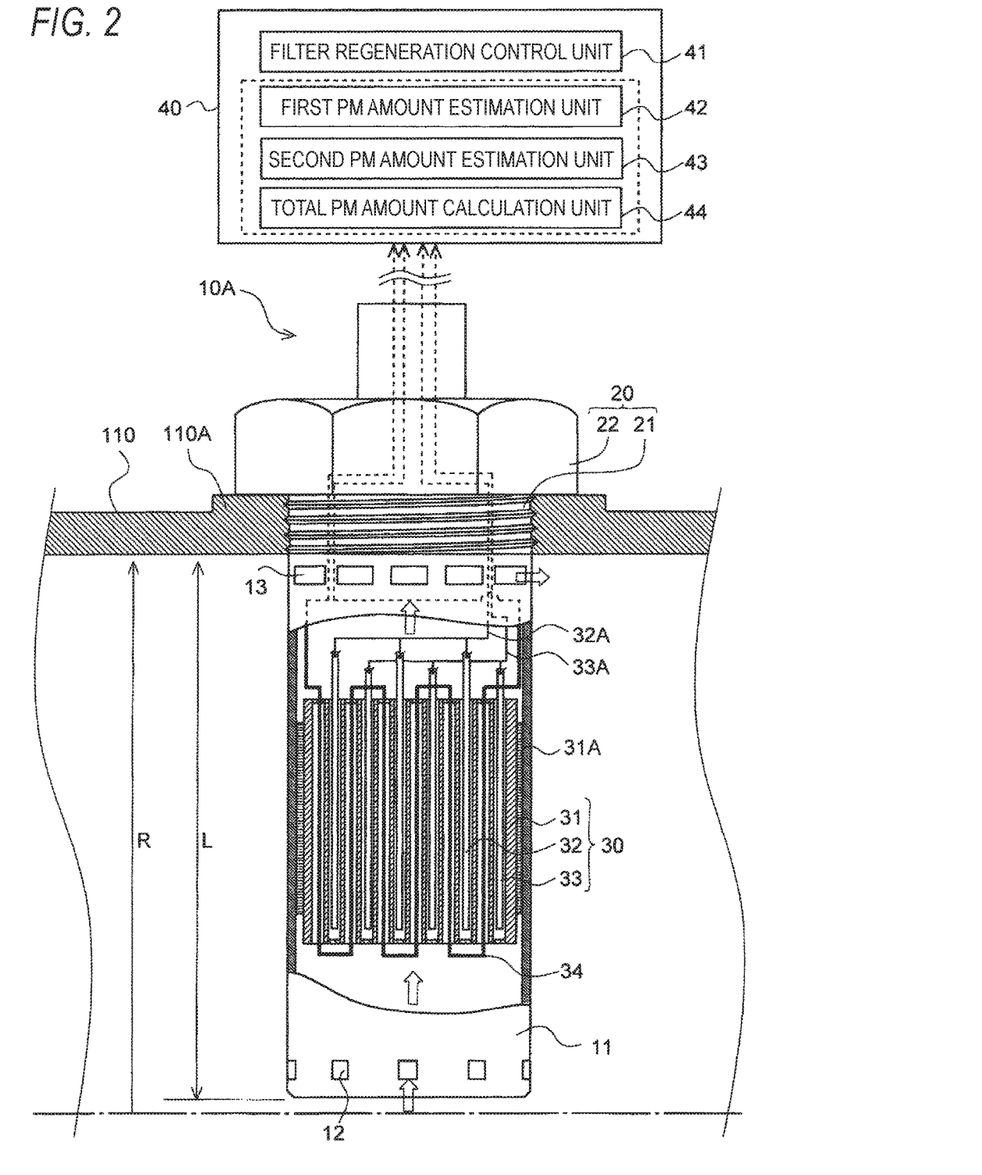
FIG. 2 is a schematic partially sectional view depicting the PM sensor of the first illustrative embodiment.

Subsequently, a detailed configuration of the PM sensor 10A in accordance with the first illustrative embodiment is described with reference to FIG. 2.

The PM sensor 10A has a case member 11 inserted in the exhaust pipe 110, a base part 20 attaching the case member 11 to the exhaust pipe 110, a sensor unit 30 accommodated in the case member 11, and a control unit 40.

The case member 11 has a bottomed cylinder shape of which a bottom side (a lower end side in the shown example) is closed. A length L of the case member 11 in a cylinder axis direction is substantially the same as a radius R of the exhaust pipe 110 so that a cylindrical wall part at the bottom side protrudes to a position close to a center of axis CL of the exhaust pipe 110. Meanwhile, in the following descriptions, the bottom side of the case member 11 is referred to as a tip end-side, and an opposite side to the bottom side is referred to as a base end-side of the case member 11.

A cylindrical wall part of the case member 11 at the tip end-side is provided with a plurality of inflow ports 12 arranged with an interval in a circumferential direction. Also, a cylindrical wall part of the case member 11 at the base end-side is provided with a plurality of outflow ports 13 arranged with an interval in the circumferential direction. A total opening area. $S_{12}$ of the inflow ports 12 is smaller than a total opening area $S_{13}$ of the outflow ports 13 ($S_{12}<S_{13}$). That is, an exhaust flow velocity $V_{12}$ in the vicinity of the inflow ports 12 becomes slower than an exhaust flow velocity $V_{13}$ in the vicinity of the outflow ports 13 ($V_{12}<V_{13}$), so that a pressure $P_{12}$ at a side of the inflow ports 12 becomes higher than a pressure $P_{13}$ at a side of the outflow ports 13 ($P_{12}>P_{13}$). Thereby, the exhaust gas smoothly flows into the case member 11 from the inflow ports 12, and the exhaust gas in the case member 11 smoothly flows out from the outflow ports 13 into the exhaust pipe 110.

The base part 20 has a male screw portion 21 and a nut portion 22. The male screw portion 21 is provided at a base end portion of the case member 11 and closes an opening of the case member 11 at the base end-side. The male screw portion 21 is screwed with a female screw portion of a boss part 110A formed in the exhaust pipe 110. The nut portion 22 is a hexagonal nut, for example, and is fixed to an upper end portion of the male screw portion 21. The male screw portion 21 and the nut portion 22 are formed with through-holes (not shown) into which conductive lines 32A, 33A and the like (which will be described later) are inserted.

The sensor unit 30 has a filter member 31, a plurality of pairs of electrodes 32, 33 and an electrical heater 34.

The filter member 31 is formed by alternately plugging upstream and downstream sides of a plurality of cells forming a lattice-shaped exhaust flow path divided by partition walls of porous ceramics. The filter member 31 is held on an inner peripheral surface of the case member 11 via a cushion member 31A with a flow path direction of the cells being made to be substantially parallel with an axis direction (an upper and lower direction in FIG. 2) of the case member 11. PM in the exhaust gas introduced into the case member 11 from the inflow ports 12 is trapped in partition wall surfaces or fine holes as the exhaust gas flows from the cells plugged at the downstream side thereof into the cells plugged at the upstream side thereof. In the following descriptions, the cell plugged at the downstream side thereof is referred to as a measurement cell and the cell plugged at the upstream side thereof is referred to as an electrode cell.

The electrodes 32, 33 are conductive metal lines, for example, and are alternately inserted from the downstream side (non-plugging side) to the electrode cells facing each other with the measurement cell being interposed therebetween, thereby forming a capacitor. The electrodes 32, 33 are respectively connected to an electrostatic capacitance detection circuit (not shown) embedded in the control unit 40, via the conductive lines 32A, 33A.

The electrical heater 34 is an example of the regeneration means of the present invention, and is formed of a heating wire or the like, for example. The electrical heater 34 generates heat to heat the measurement cells by energization, thereby executing so-called filter regeneration of combusting and removing the PM accumulated in the measurement cells. Therefore, the electrical heater 34 is preferably formed with being bent into a continuous S-shape, and linear portions thereof parallel with each other are inserted into the respective measurement cells along the flow path.

The control unit 40 performs a variety of controls and includes a CPU, a ROM, a RAM, an input port, an output port and the like, which are well known. Also, the control unit 40 has a filter regeneration control unit 41, a first PM amount estimation unit 42, a second PM amount estimation unit 43 and a total PM amount calculation unit 44, as respective functional elements. The functional elements are included in the control unit 40, which is the integrated hardware, but can also be provided for separate hardware.

The filter regeneration control unit 41 is an example of the regeneration means of the present invention, and executes filter regeneration control of turning on (energizing) the electrical heater 34 in accordance with an electrostatic capacitance Cp between the respective electrodes 32, 33 which is detected by the electrostatic capacitance detection circuit (not shown). The electrostatic capacitance Cp between the electrodes 32, 33 is expressed by a following equation (1), in which a dielectric constant of a medium between the electrodes 32, 33 is assumed to be c, a surface area of the electrodes 32, 33 is assumed to be S, and a distance between the electrodes 32, 33 is assumed to be d.

$$Cp = \sum \left( \varepsilon \times \frac{S}{d} \right) \qquad \text{[equation 1]}$$

Figure 3:
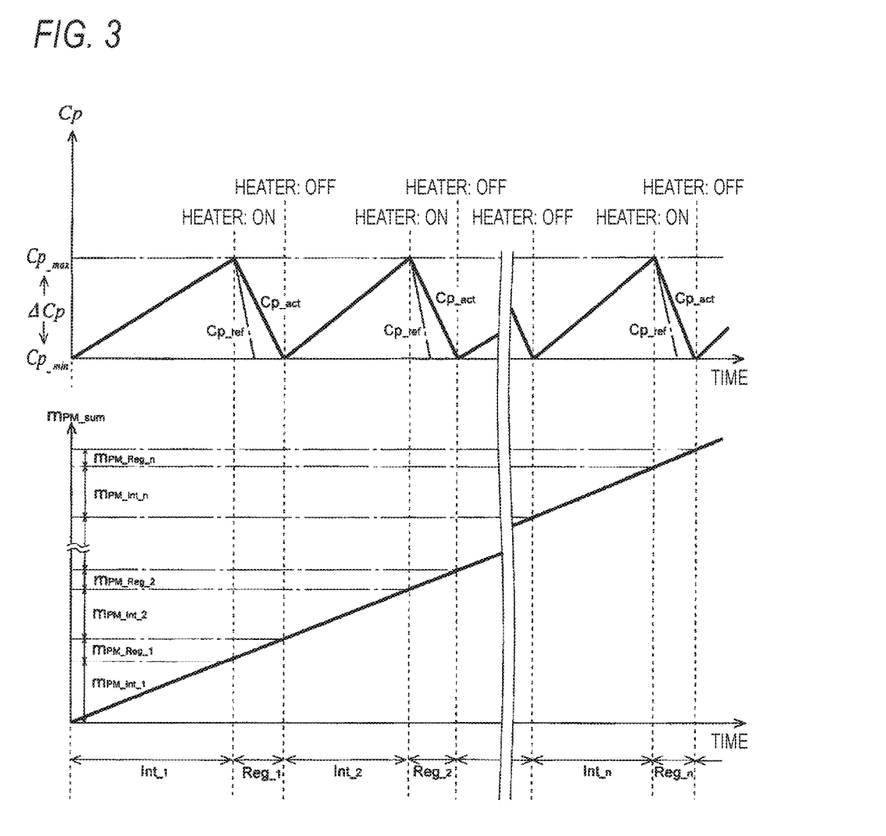
FIG. 3 is timing charts illustrating filter regeneration and integration of PM amounts in accordance with the first illustrative embodiment.

In the equation (1) the surface area S of the electrodes 32, 33 is constant, and when the dielectric constant ε and the distance d are changed by the PM trapped in the measurement cells, the electrostatic capacitance Cp correspondingly changes. That is, the electrostatic capacitance Cp between the electrodes 32, 33 and an amount of the PM accumulated in the filter member 31 have a proportional relation. As shown in FIG. 3, when the electrostatic capacitance Cp between the electrodes 32, 33 reaches a predetermined electrostatic capacitance upper limit threshold $C_{P\_max}$, which indicates the upper limit amount of the accumulated PM, the filter regeneration control unit 41 starts filter regeneration of turning on the electrical heater 34. The filter regeneration continues until the electrostatic capacitance Cp is lowered to a predetermined electrostatic capacitance lower limit threshold $C_{P\_min}$, which indicates that the PM is completely removed.

The first PM amount estimation unit 42 is an example of the estimation means of the present invention, and estimates and calculates an amount of PM (hereinafter, referred to as interval period PM amount $m_{PM\_Int\_n}$), which is trapped in the filter member 31 during each regeneration interval period from an end of the filter regeneration to a start of a next filter regeneration, based on an electrostatic capacitance change amount ΔCp, between the electrodes 32, 33 (refer to FIG. 3). More specifically, the first PM amount estimation unit 42 sequentially calculates the interval period PM amounts $m_{PM\_Int\_n}$, based on a following equation (2) of multiplying the electrostatic capacitance change amount $\Delta Cp_n$ between the electrodes 32, 33, which is detected during the regeneration interval period by the electrostatic capacitance detection circuit (not shown), by a linear coefficient β.

$$m_{PM\_Int\_n} = \beta \cdot \Delta Cp_n \qquad \text{[equation 2]}$$

The interval period PM amounts $m_{PM\_Int\_n}$, which are calculated by the first PM amount estimation unit 42, are sequentially output to the total PM amount calculation unit 44 which will be described later.

The second PM amount estimation unit 43 is a part of the estimation means of the present invention, and estimates PM amounts (hereinafter, referred to as regeneration period PM amounts $m_{PM\_Reg\_n}$), which are trapped in the filter member 31 during the filter regeneration execution period, based on the electrostatic capacitance reduction amount between the electrodes 32, 33 (refer to FIG. 3). Hereinafter, a method of estimating the regeneration period PM amounts $M_{PM\_Reg\_n}$ is described in detail.

In a storage unit of the control unit 40, the electrostatic capacitance reduction amount between the electrodes 32, 33, which has been measured in advance by a test or the like when the filter regeneration has been executed in a state where an exhaust gas (new PM) is not flowing into the filter member 31, is stored as a reference reduction amount $Cp_{\_ref}$. The regeneration period PM amount $m_{PM\_Reg\_n}$ (new PM amount), which is trapped in the filter member 31 as the exhaust gas flows into the filter member 31 during the execution of the filter regeneration, is expressed by a following equation (3) of multiplying a deviation between an actual electrostatic capacitance reduction amount $Cp_{act}$ between the electrodes 32, 33, which is detected during the filter regeneration, and the reference reduction amount $Cp_{\_ref}$ by a linear coefficient α.

$$m_{PM\_Reg\_n} = \alpha \cdot (Cp_{\_act} - Cp_{\_ref}) \qquad \text{[equation 3]}$$

The second PM amount estimation unit 43 calculates in real time the regeneration period PM amounts $M_{PM\_Reg\_n}$, based on the equation (3). The regeneration period PM amounts $m_{PM\_Reg\_n}$, which are calculated by the second PM amount estimation unit 43, are sequentially output to the total PM amount calculation unit 44 which will be described later.

The total PM amount calculation unit 44 is an example of the estimation means of the present invention, and calculates in real time a total PM amount $m_{PM\_sum}$ in the exhaust gas discharged from the engine 100, based on a following equation (4) of alternately and sequentially integrating the interval period PM amounts $m_{PM\_Int\_n}$ input from the first PM amount estimation unit 42 and the regeneration period PM amounts $m_{PM\_Reg\_n}$ input from the second PM amount estimation unit 43.

$$m_{PM\_sum} = m_{PM\_Int\_1} + m_{PM\_Reg\_1} + m_{PM\_Int\_2} + m_{PM\_reg\_2} + \cdots + m_{PM\_Int\_n} + m_{PM\_Reg\_n} \qquad \text{[equation 4]}$$

In this way, according to the first illustrative embodiment, during the regeneration interval period $Int\_n$, the interval period PM amounts $m_{PM\_Int\_n}$ are calculated based on the electrostatic capacitance change amount $\Delta Cp_n$ between the electrodes 32, 33, which is more sensitive than the electrical resistance value, and during the filter regeneration period $Reg\_n$, the regeneration period PM amounts $m_{PM\_Reg\_n}$ are calculated based on the electrostatic capacitance reduction amount between the electrodes 32, 33 having favorable sensitivity, and the PM amounts are sequentially integrated. Thereby, it is possible to estimate the PM amount in the exhaust gas, which is discharged from the engine 100, in real time and with high precision.

Hereinafter, operational effects of the PM sensor 10A of the first illustrative embodiment are described.

in an electrical resistance-type PM sensor that estimates the PM amount based on an electrical resistance value between the electrodes, during a regeneration period of the electrodes and a period until the respective electrodes are connected by the PM, the electrical resistance value does not change. Therefore, it is not possible to estimate in real time a PM amount in the exhaust gas.

In contrast, the PM sensor 10A of the first illustrative embodiment estimates the PM amounts based on the electrostatic capacitance change amount between the electrodes 32, 33 having favorable sensitivity during the regeneration interval period, estimates the PM amounts based on the electrostatic capacitance reduction amount between the electrodes 32, 33 having favorable sensitivity during the filter regeneration period, and sequentially integrates the estimated PM amounts, thereby calculating the PM amount in the exhaust gas. Therefore, according to the PM sensor 10A of the first illustrative embodiment, it is possible to estimate the PM amount in the exhaust gas discharged from the engine 100 with high precision and in real time.

Also, in the electrical resistance-type PM sensor in which the PM is attached to each electrode, there is a possibility that some of the PM may be detached from the electrodes in a driving state where the exhaust flow rate increases. In this case, it is not possible to ensure the estimation precision of the PM amount. In contrast, the PM sensor 10A of the first illustrative embodiment reliably traps the PM in the exhaust gas by the filter member 31. Therefore, according to the PM sensor 10A of the first illustrative embodiment, it is possible to effectively ensure the estimation precision of the PM amount even in the driving state where the exhaust flow rate increases.

Also, according to the PM sensor 10A of the first illustrative embodiment, the case member 11 that accommodates therein the sensor unit 30 is configured so that the tip end portion thereof protrudes to the position in the exhaust pipe 10, which is close to the center of axis CL at which the exhaust flow velocity is highest. The cylindrical wall part of the case member 11 at the tip end-side is provided with the inflow ports 12 for introducing the exhaust gas into the case member 11. Also, the cylindrical wall part of the case member 11 at the base end-side is provided with the outflow ports 13 of which an opening area is greater than the inflow ports 12. That is, according to the PM sensor 10A of the first illustrative embodiment, the inflow ports 12 are arranged in the vicinity of the center of axis CL of the exhaust pipe 110 at which the exhaust flow velocity is high and the opening area of the outflow ports 13 is made to be great, so that it is possible to secure a high static pressure difference between the inflow ports 12 and the outflow ports 13. Thereby, it is possible to effectively promote the flow of the exhaust gas passing through the sensor unit 30.

[Second Illustrative Embodiment]

Figure 4:
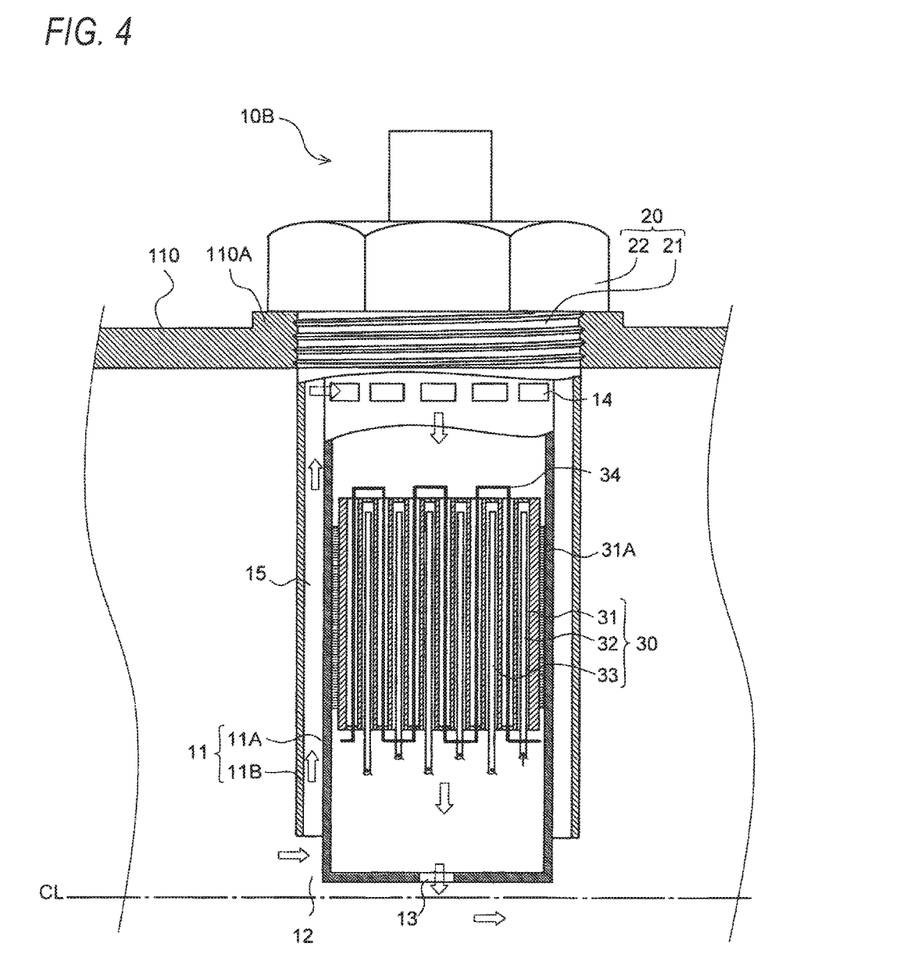
FIG. 4 is a schematic partially sectional view depicting a PM sensor of a second illustrative embodiment.

Subsequently, a PM sensor 10 B in accordance with a second illustrative embodiment is described in detail with reference to FIG. 4. In the PM sensor 10 B of the second illustrative embodiment, the case member 11 of the PM sensor 10A of the first illustrative embodiment has a double pipe structure. Since the other constitutional elements have the same structures, the detailed descriptions thereof are omitted. Also, the conductive line 324, 334 and the control unit 40 are not shown.

The case member 11 of the second illustrative embodiment has a cylindrical bottomed inner case part 11A and a cylindrical outer case part 119 that surrounds a cylindrical outer peripheral surface of the inner case part 11A.

The inner case part 11A has an axial length greater than the outer case part 11B so that a tip end-side protrudes beyond the outer case part 11B. Also, a bottom part of the inner case part 11A is provided with an outflow port 13 for enabling the exhaust gas in the inner case part 11A to flow into the exhaust pipe 110. Further, a cylindrical wall part of the inner case part 11A at a base end-side is provided with a plurality of passage ports 14 arranged with an interval in a circumferential direction. The passage ports 14 enable the exhaust gas in a flow path 15 defined by an outer peripheral surface of the inner case part 11A and an inner peripheral surface of the outer case part 11B to flow into the inner case part 11A.

A downstream end of the flow path 15 is formed with a circular ring-shaped inflow port 12 defined by the cylindrical wall part of the inner case part 11A at the tip end-side and the tip end portion of the outer case part 11B. An opening area $S_{12}$ of the inflow port 12 is formed to be smaller than an opening area $S_{13}$ of the outflow port 13 ($S_{12} < S_{13}$).

That is, the exhaust gas flowing through the exhaust pipe 110 contacts with the cylindrical wall surface of the inner case part 11A protruding more than the outer case part 11B, and is smoothly introduced into the flow path 15 from the inflow port 12 arranged in the vicinity of the center of axis CL of the exhaust pipe 110. Also, the exhaust gas flowing through the flow path 15 is introduced into the inner case part 11A from the passage ports 14, passes through the filter member 31, and then smoothly flows out from the outflow port 13 arranged in the vicinity of the center of axis CL of the exhaust pipe 110 into the exhaust pipe 110. In this way, according to the PM sensor 10B of the second illustrative embodiment, the inflow port 12 and the outflow port 13 are arranged in the vicinity of the center of axis CL at which the exhaust flow velocity is highest in the exhaust pipe 110, so that it is possible to effectively increase the exhaust flow rate passing through the filter member 31.

[Third Illustrative Embodiment]

Subsequently, a PM sensor in accordance with a third illustrative embodiment is described in detail with reference to FIG. 5. In the PM sensor of the third illustrative embodiment, the sensor unit 30 of the first illustrative embodiment has a stack-type structure. Since the other constitutional elements have the same structure, the detailed descriptions and illustrations thereof are omitted.

Figure 5:
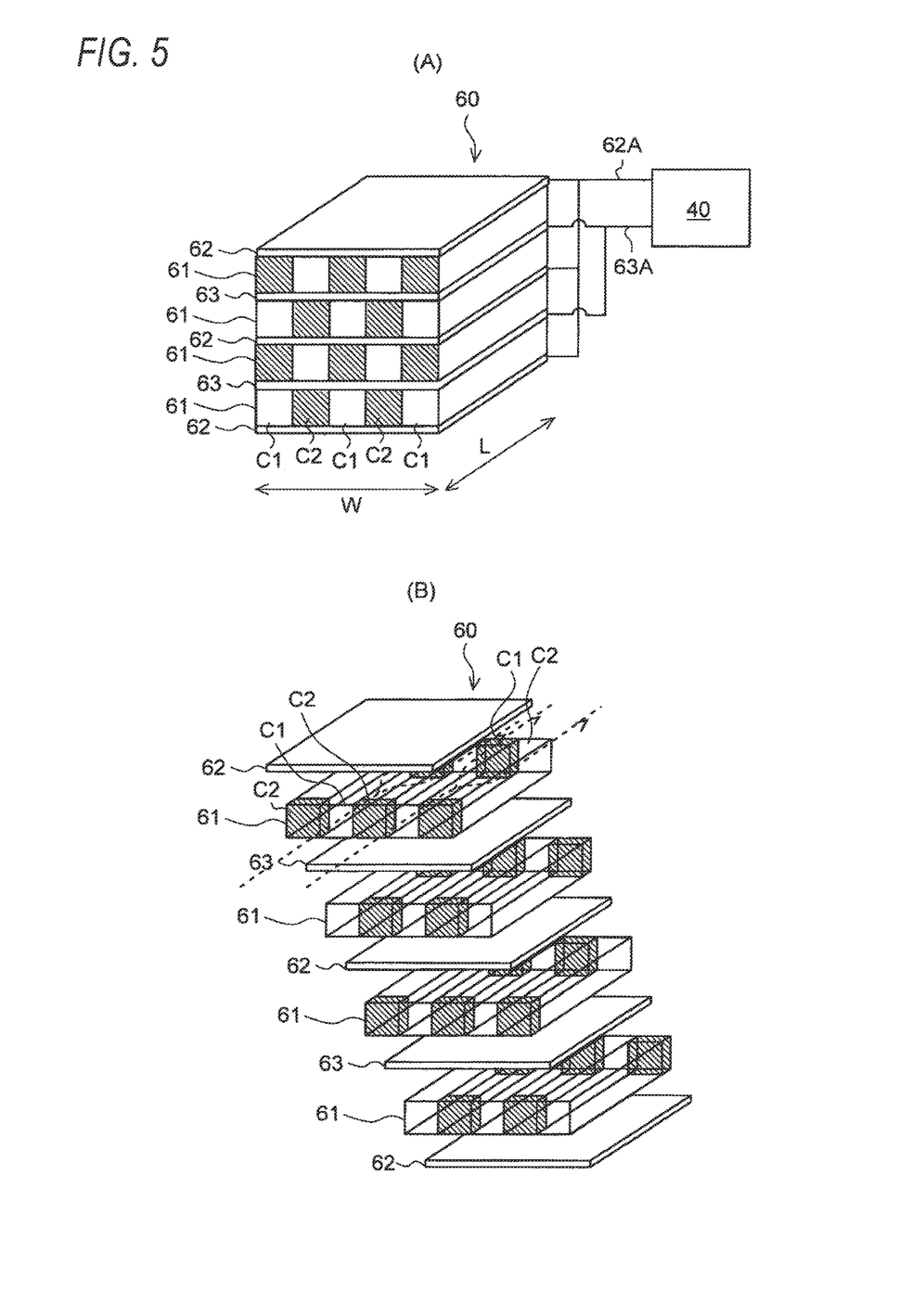
FIG. 5(A) is a schematic perspective view of a PM sensor of a third illustrative embodiment.
FIG. 5(B) is a schematic exploded perspective view of the PM sensor of the third illustrative embodiment.

(A) of FIG. 5 is a perspective view of a sensor unit 60 of the third illustrative embodiment and (B) of FIG. 5 is an exploded perspective view of the sensor unit 60. The sensor unit 60 has a plurality of filter layers 61 and a plurality of first and second electrode plates 62, 63.

The filter layer 61 has a cuboid shape where upstream and downstream sides of a plurality of cells divided by partition walls of porous ceramics or the like and forming an exhaust flow path are alternately plugged and the cells are arranged in parallel in one direction. The PM included in the exhaust gas is trapped in the partition wall surfaces or fine holes of the cells C1 as the exhaust gas flows from the cells C1 of which downstream sides are plugged into the cells C2 of which upstream sides are plugged, as shown with the dotted arrow in (B) of FIG. 5. In the following descriptions, a cell flow path direction is referred to as a longitudinal direction (an arrow L in (A) of FIG. 5) of the sensor unit 60, and a direction perpendicular to the cell flow path direction is referred to as a width direction (an arrow W in (A) of FIG. 5) of the sensor unit 60.

The first and second electrode plates 62, 63 are conductive members having a flat plate shape, for example, and external dimensions thereof in the longitudinal direction L and the width direction W are substantially the same as the filter layer 61. The first and second electrode plates 62, 63 are alternately stacked with the filter layers 61 being interposed therebetween, and are respectively connected to the electrostatic capacitance detection circuit (not shown) embedded in the control unit 40 via conductive lines 62A, 63A.

That is, the first electrode plates 62 and the second electrode plates 63 are arranged to face each other and the filter layers 61 are interposed between the electrode plates 62, 63, so that the entire cells C1 form a capacitor. In this way, according to the PM sensor of the third illustrative embodiment, the entire cells C1 are configured as the capacitor by the electrode plates 62, 63 having a flat plate shape, so that it is possible to effectively secure an electrode surface area S and to increase an absolute value of the detectable electrostatic capacitance. Also, the distance d between the electrodes is a pitch of the cells and is uniform, so that it is possible to effectively suppress the non-uniformity of the initial electrostatic capacitance.

In the meantime, in a case of combusting and removing the PM accumulated in the cells C1, a voltage may be directly applied to the electrode plates 62, 63, or a heater board or the like (not shown) may be provided between the filter layer 61 and the electrode plates 62, 63.

[Others]

The present invention is not limited to the above illustrative embodiments and the illustrative embodiments can be appropriately changed without departing from the spirit of the present invention.

Figure 6:
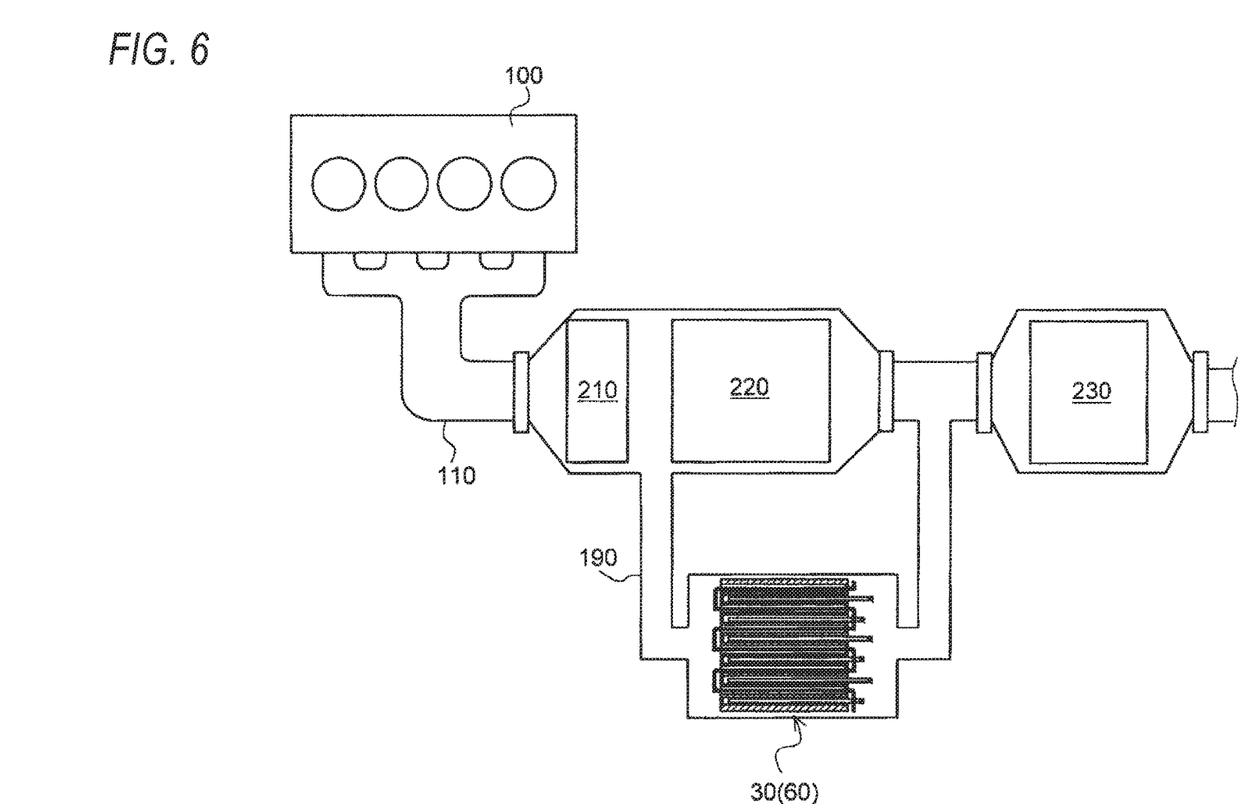
FIG. 6 is a schematic configuration view depicting an example of the exhaust system to which a PM sensor of another illustrative embodiment is applied.

For example, as shown in FIG. 6, a bypass pipe 190 branching from between the oxidation catalyst 210 and the DPF 220 and joining to an upstream side of the NOx purification catalyst 230 may be connected to the exhaust pipe 110 and the sensor unit 30 of the first illustrative embodiment or the sensor unit 60 of the third illustrative embodiment may be arranged in the bypass pipe 190.

Figure 7:
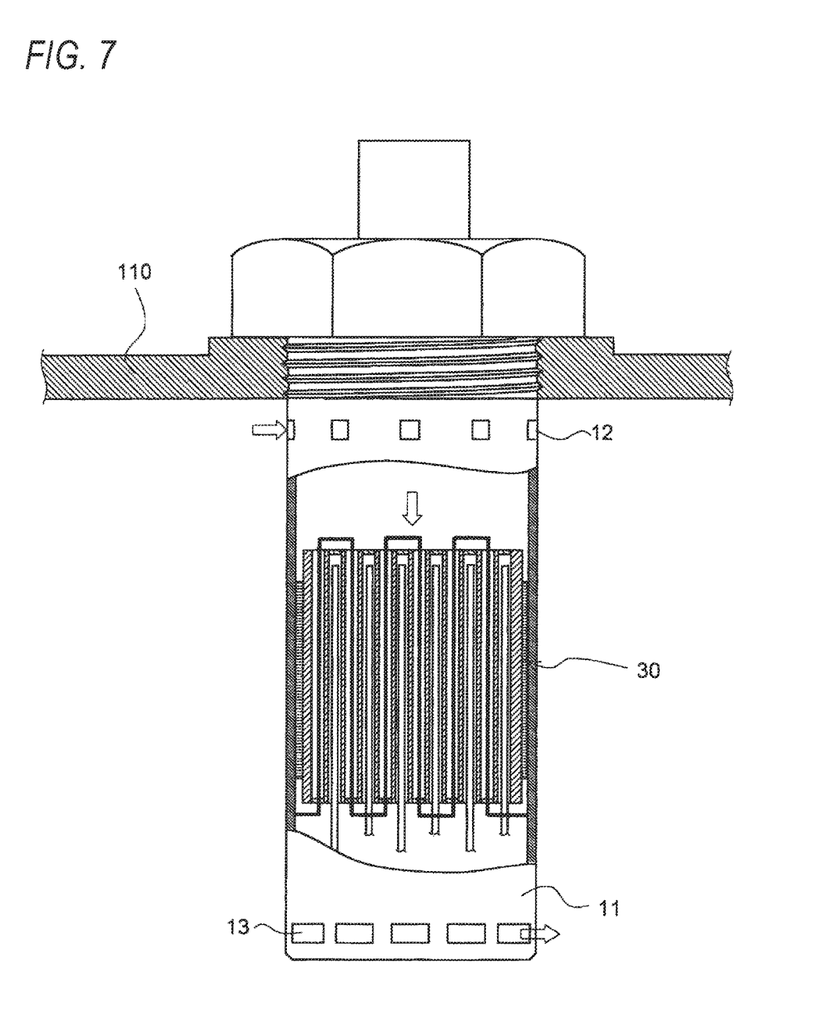
FIG. 7 is a schematic partially sectional view depicting a PM sensor of another illustrative embodiment.

Also, as shown in FIG. 7, in the first illustrative embodiment (or the second illustrative embodiment), the positions of the inflow ports 12 and the outflow ports 13 may be interchanged to reverse the flowing direction of the exhaust gas that is introduced into the case member 11. In this case, the filter member 31 has to be accommodated with being reversed in the case member 11.

The invention claimed is:

1. A sensor comprising:
   a porous filter member including a plurality of cells that traps particulate matter in exhaust gas;
   at least a pair of electrode members arranged to face each other with the cell being interposed therebetween and forming a capacitor;
   a regeneration unit that executes, when a predetermined amount of particulate matter has accumulated in the cell, filter regeneration of heating the cell to combust and remove the accumulated particulate matter;
   a storage unit that stores therein a reference reduction amount, which is an electrostatic capacitance reduction amount between the pair of electrode members in a case where the filter regeneration has been executed by the regeneration unit in a state where the exhaust gas including the particulate matter is not flowing into the filter member; and an estimation unit that estimates a particulate matter amount included in the exhaust gas based on an actual electrostatic capacitance change amount between the pair of electrode members during a regeneration interval period from an end of the filter regeneration by the regeneration unit to a start of a next filter regeneration, and estimates the particulate matter amount included in the exhaust gas based on a difference between an actual electrostatic capacitance reduction amount between the pair of electrode members and the reference reduction amount during a filter regeneration period by the regeneration unit.

2. The sensor according to claim 1, wherein the estimation unit estimates in real time the particulate matter amount in the exhaust gas by sequentially integrating a particulate matter amount estimated based on the actual electrostatic capacitance change amount between the pair of electrode members during the regeneration interval period and the particulate matter amount estimated based on the difference between the actual electrostatic capacitance reduction amount between the pair of electrode members and the reference reduction amount during the filter regeneration period.

3. The sensor according to claim 2, wherein the regeneration unit includes a heating wire inserted into the cells and generating heat by energization.

4. The sensor according to claim 2, wherein the filter member is a filter layer in which the plurality of cells is arranged in parallel in one direction, the pair of electrode members is first and second electrode plates having a flat plate shape and arranged to face each other with the filter layer being interposed therebetween, the regeneration unit includes a heater board having a flat plate shape and generating heat by energization, and the heater board is provided between the first electrode plate and the filter layer or between the second electrode plate and the filter layer.

5. The sensor according to claim 1, wherein the regeneration unit includes a heating wire inserted into the cells and generating heat by energization.

6. The sensor according to claim 1, wherein the filter member is a filter layer in which the plurality of cells is arranged in parallel in one direction, the pair of electrode members is first and second electrode plates having a flat plate shape and arranged to face each other with the filter layer being interposed therebetween, the regeneration unit includes a heater board having a flat plate shape and generating heat by energization, and the heater board is provided between the first electrode plate and the filter layer or between the second electrode plate and the filter layer.

* * * * *